(12) United States Patent
O'Donnell et al.

(10) Patent No.: US 11,344,522 B2
(45) Date of Patent: May 31, 2022

(54) NUTRITIONAL PRODUCT

(71) Applicants: VITAFLO (INTERNATIONAL) LTD, Liverpool (GB); UCL BUSINESS PLC, London (GB)

(72) Inventors: Maura O'Donnell, Hightown (GB); Bridget Lambert, Liverpool (GB); Patricia Wallis, Liverpool (GB); Patricia Rutherford, Liverpool (GB); Simon Heales, London (GB); Sean-David Hughes, London (GB); Helen Cross, London (GB); Simon Eaton, London (GB)

(73) Assignees: Vitaflow (International) Ltd, Liverpool (GB); UCL Business PLC, London (GB)

( * ) Notice: Subject to any disclaimer, the term of this patent is extended or adjusted under 35 U.S.C. 154(b) by 797 days.

(21) Appl. No.: 14/406,957

(22) PCT Filed: Jun. 14, 2013

(86) PCT No.: PCT/GB2013/051561
§ 371 (c)(1),
(2) Date: Dec. 10, 2014

(87) PCT Pub. No.: WO2013/186570
PCT Pub. Date: Dec. 19, 2013

(65) Prior Publication Data
US 2015/0164840 A1 Jun. 18, 2015

Related U.S. Application Data

(60) Provisional application No. 61/704,277, filed on Sep. 21, 2012.

(30) Foreign Application Priority Data

Jun. 15, 2012 (GB) .................................. 1210699

(51) Int. Cl.
*A61K 31/20* (2006.01)
*A61K 33/12* (2006.01)
*A23L 33/12* (2016.01)
*A61K 31/19* (2006.01)
*A61K 31/70* (2006.01)
*A61K 38/02* (2006.01)

(52) U.S. Cl.
CPC .............. *A61K 31/20* (2013.01); *A23L 33/12* (2016.08); *A61K 31/19* (2013.01); *A61K 31/70* (2013.01); *A61K 38/02* (2013.01); *A23V 2002/00* (2013.01)

(58) Field of Classification Search
CPC ..................................................... A61K 31/20
See application file for complete search history.

(56) References Cited

U.S. PATENT DOCUMENTS

| | | | |
|---|---|---|---|
| 2007/0135376 A1 | 6/2007 | Henderson | |
| 2008/0009467 A1* | 1/2008 | Henderson | ........... A61K 31/225 |
| | | | 514/129 |
| 2010/0204498 A1 | 8/2010 | Iinuma et al. | |
| 2011/0200734 A1 | 8/2011 | Nasaka et al. | |
| 2013/0303616 A1 | 11/2013 | Williams et al. | |

FOREIGN PATENT DOCUMENTS

| | | |
|---|---|---|
| JP | 2002536304 A | 10/2002 |
| JP | 2003531857 A | 10/2003 |
| JP | 2012097038 | 5/2012 |
| WO | WO2010052847 | 5/2010 |
| WO | 2011040342 A1 | 4/2011 |

OTHER PUBLICATIONS

Sills, et al., Archives of Disease in Childhood, 1986, 61, 1173-1177.*
Likhodii et al., Epilepsia, 41 ( 11):1400-1410, 2000 (Year: 2000).*
Sills et al., Archives of Disease in Childhood, 1986, 61, 1173-1177 (Year: 1986).*
Neal, et al., Epilepsia, 50(5):1109-1117, 2009 (Year: 2009).*
P. Chang et al./ Neuropharmacology 69 (2013) 105-114 (Year: 2013).*
Chang et al. "The antiepileptic drug valproic acid and other medium-chain fatty acids acutely reduce phosphoinositide levels independently of inositol in Dictyostelium" Disease Models & Mechanisms, vol. 5, 2012, pp. 115-124.
Chang et al. "Seizure control by ketogenic diet-associated medium chain fatty acids" Neuropharmacology, vol. 69, 2013, pp. 105-114.
Nazari et al. "Fatty acid analysis of Iranian junk food, dairy, and bakery products: Special attention to trans-fats" Journal of Research in Medical Sciences, vol. 17, 2012, pp. 952-957.
Alonso et al. "Fatty Acid Composition of Caprine Milk: Major, Branched-Chain, and Trans Fatty Acids" Journal of Dairy Science, vol. 82, No. 5, 1999, pp. 878-884.
Wlaz et al. "Anticonvulsant profile of caprylic acid, a main constituent of the medium-chain triglyceride (MCT) ketogenic diet, in mice" Neuropharmacology, vol. 62, 2012, pp. 1882-1889.
Sills et al. "Role of octanoic and decanoic acids in the control of seizures" Archives of Disease in Childhood, 1986, vol. 61, pp. 1173-1177.
Japanese Office Action—Patent Application No. P2015-516688—dated Feb. 21, 2017—4 pages (English Translation).
Japanese Office Action—Patent Application No. P2015-516638—dated Feb. 21, 2017—4 pages.
Gong et al., "Effect of medium-chain caprylic and capric acids on glucose metabolism in mice with diabetes mellitus", J Chinese PLA Postgrad Med Sch, Feb. 2012, pp. 108-109 and 113, English abstract.
"New release of 3 types of 'Enelprin' for elderly people who can quickly supply energy", Nisshin Oillio, May 9, 2012, webpage available at: http://www.nisshin-oillio.com/company/news/archive/2012/20120509_141941.shtml.

(Continued)

*Primary Examiner* — Yong S. Chong
(74) *Attorney, Agent, or Firm* — K&L Gates LLP

(57) ABSTRACT

The present invention generally relates to the field of dietary therapies for treating disorders associated with mitochondrial dysfunction, including epilepsy.

33 Claims, 5 Drawing Sheets

(56) References Cited

OTHER PUBLICATIONS

"Enelrin strawberry taste", Nisshin Oillio, webpage available at: https://shop.nisshin.oilliogroup.com/products/detail/24121.

European Office Action for corresponding European Application No. 13730925.8, dated Oct. 17, 2018; (4 pages).

Australian Office Action for corresponding Australian Application No. 2018200433 dated Sep. 10, 2018, (5 pages).

Hattatsu, Brain and Development, vol. 42, Issue No. 2, 2010, pp. 124-129.

Jones et al., "Accumulation of 3-Hydroxy-Fatty Acids in the Culture Medium of Long-Chain L-3-Hydroxyacyl CoA Dehydrogenase (LCHAD) and Mitochondrial Trifunctional Protein-Deficient Skin Fibroblasts: Implications for Medium Chain Triglyceride Dietrary Treatment of LCHAD Deficiency", Pediatric Research, vol. 53, Issue No. 5, 2003, pp. 783-787.

Jones et al., "Effects of Odd-Numbered Medium-Chain Fatty Acids on the Accumulation of Long-Chain 3-Hydroxy-Fatty Acids in Long-Chain L-3-Hydroxyacyl CoA Dehydrogenase and Mitochondrial Trifunctional Protein Deficient Skin Fibroblasts", Molecular Genetics and Metabolism, vol. 81, 2004, pp. 96-99.

Fushiki et al., "Swimming Endurance Capacity of Mice is Increased by Chronic Consumption of Medium-Chain Triglycerides", The Journal of Nutrition, vol. 125, Issue No. 3, 1995, pp. 531-539.

Turner et al., "Enhancement of Muscle Mitochondrial Oxidative Capacity and Alterations in Insulin Action are Lipid Species Dependent", Diabetes, vol. 58, Issue No. 11, 2009, pp. 2547-2554.

Japan Patent Office Communication Application No. P2021-050443, Dispatch No. 022610, Dispatch Date Jan. 25, 2022, 9 pages.

\* cited by examiner

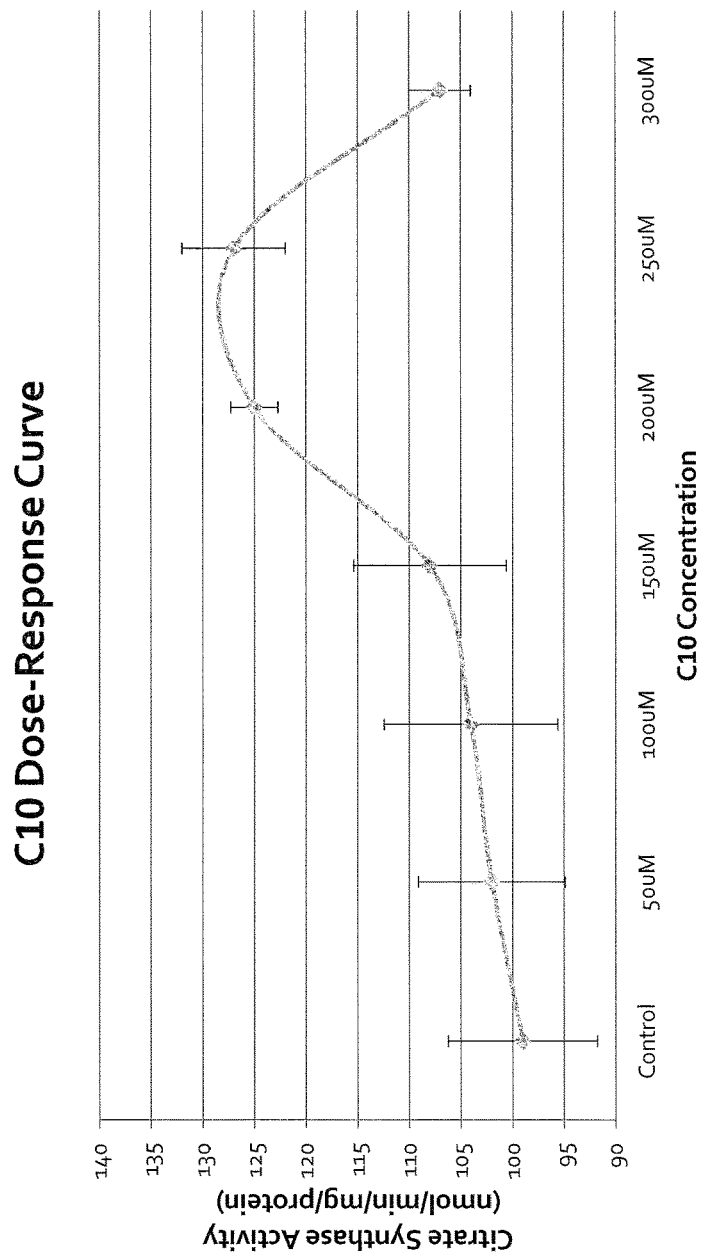
Figure 1. Dose-response curve over a 6 day incubation period.

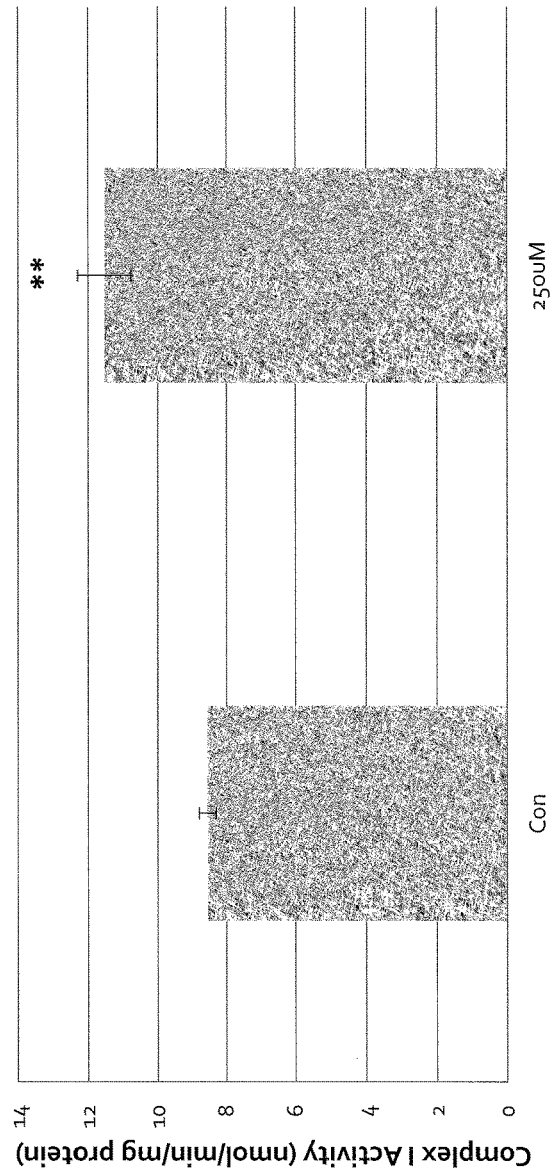
Figure 2
Effect of 250µM C10 for 6 Days on Complex I Activity
Control = 8.8 ± 0.25; 250µM = 12 ± 0.77. Results ± SEM. n = 5.
** p < 0.002.

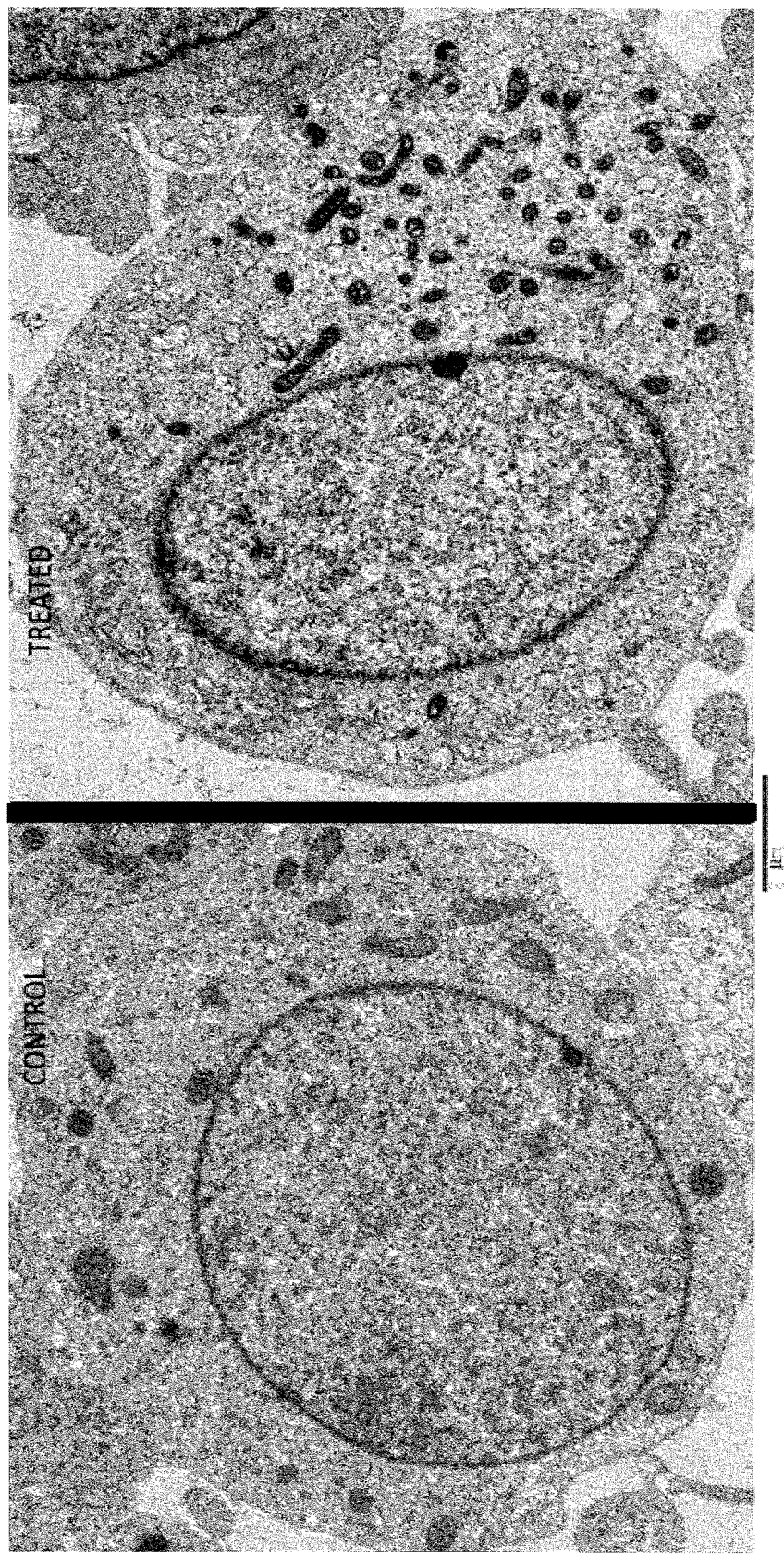

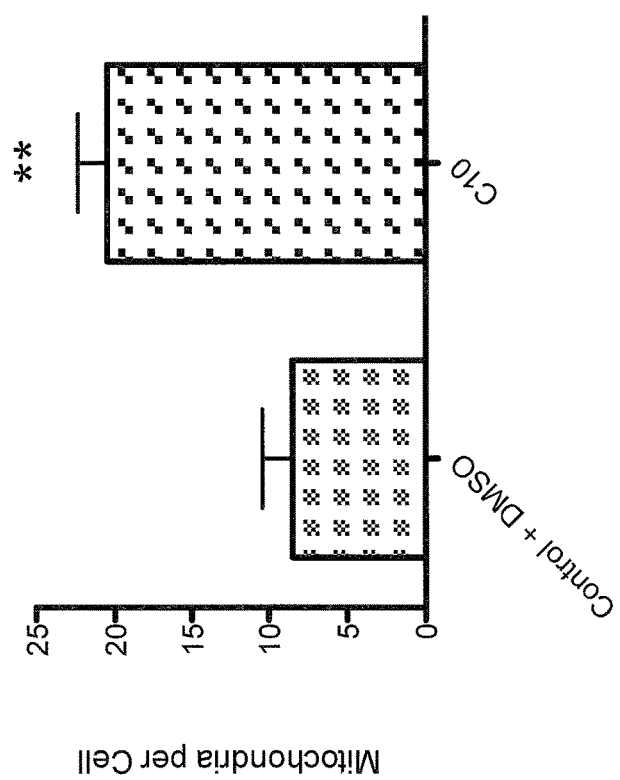

NUTRITIONAL PRODUCT

CROSS REFERENCE TO RELATED APPLICATIONS

The present application is a National Stage of International Application No. PCT/GB2013/051561, filed on Jun. 14, 2013, which claims priority to Great Britain Patent Application No. 1210699.3, filed Jun. 15, 2012, and U.S. Provisional Application No. 61/704,277, filed Sep. 21, 2012, the entire contents of which are being incorporated herein by reference.

FIELD OF THE INVENTION

The present invention generally relates to the field of dietary therapies for treating disorders associated with mitochondrial dysfunction, including epilepsy.

BACKGROUND OF THE INVENTION

Epilepsy covers a broad range of neurological disorders that are characterised by seizures. Seizures result from abnormal neuronal activity and manifest in a number of ways, including convulsions and loss of awareness. In many cases epilepsy can be managed by the use of anti-convulsive medication. However for a proportion of patients with epilepsy, treatment with conventional drugs can have minimal effect upon seizure activity. Although surgery is an option for treating patients suffering from certain seizures, for many individuals successful management can be achieved less invasively with the ketogenic diet.

Ketogenic diets have a high fat and low carbohydrate content with sufficient protein for growth and repair; vitamin and mineral levels are typically inadequate and may be required to be provided as supplements. Ketogenic diets function by forcing the body to metabolise fat instead of carbohydrate as its energy source. Under low dietary carbohydrate conditions, fats are broken down into fatty acids and ketone bodies in the liver, and these compounds are utilised in further metabolic pathways for generating adenosine triphosphate (ATP) as a chemical energy source.

Studies have shown a clear benefit of the ketogenic diet in treating intractable epilepsy in children and adults. Short-term trials have demonstrated that approximately half of those studied had at least a 50% reduction in seizures after 6 months, and approximately one third reached at least a 90% reduction. In certain cases, the ketogenic diet is sufficiently effective to enable a reduction in the levels of prescribed anti-epileptic medication and also to improve quality of life.

Ketogenic diets must be strictly controlled to ensure effective seizure prevention whilst maintaining adequate nutritional value. The diets are developed and optimised on a case-by-case basis under medical supervision, and all food must be carefully measured and prepared. Deviation from the diet may result in the patient experiencing renewed seizures within a short period of time.

Although clearly effective, ketogenic diets are difficult to manage in both children and adults. Current approaches to the ketogenic diet can be very restrictive and this can lead to poor compliance, particularly in adults. Furthermore, such diets can result in a number of side-effects (including problems of the digestive system, increased serum lipid levels, drowsiness, poor growth and increased risk of fractures), and are entirely unsuitable for certain patients. Identification of the active component(s) of the ketogenic diet responsible for suppressing seizure activity therefore has the capability to dramatically simplify treatment and improve the quality of life for a significant number of patients with epilepsy.

No one knows how the diet works. A metabolic change occurs in the body which affects brain chemistry. One theory attributes the anti-seizure effect of the diet to the ketones that the ketogenic diet produces. Ketones are the products of fat breakdown. The body normally burns glucose for energy. The body can use these ketones as a source of energy instead of glucose.

Although the biochemical basis for the effectiveness of the ketogenic diet is unclear, a number of studies have highlighted a connection with altered mitochondrial function and increased mitochondrial biogenesis [Bough, K. J. et al. *Ann. Neurol.* 60, 223-235 (2006)].

Mitochondria are organelles present in almost every cell in the body. They play pivotal roles in a number of cellular processes, most prominently in energy metabolism. Provision of energy is achieved by the integrated function of the electron transport chain (ETC), which receives reducing equivalents from key metabolic pathways such as the tricarboxylic acid (TCA) cycle and fatty acid β-oxidation.

Compromised mitochondrial function may arise through inherited or acquired mutations in both nuclear and mitochondrial DNA, and may also be acquired as a result of exposure to environmental factors. Mitochondrial dysfunction is associated with a wide range of clinical conditions, which generally affect organs with high energy requirements such as muscle, liver, kidney and brain. A paucity of energy in the brain, in the form of ATP, leads to neurological impairment that can include seizures. Indeed, mitochondrial dysfunction has been linked to certain inherited and acquired epilepsies, although it is also associated with a number of other disease states, including diabetes, dementias including Alzheimer's disease, and Parkinson's disease.

Multiple direct links exist therefore between the effects of the ketogenic diet, increased mitochondrial function and biogenesis, and alleviation of epileptic seizures. As implementation of the ketogenic diet presents a number of challenges, products which target the same biological mechanisms are clearly highly desirable.

SUMMARY OF THE INVENTION

The ketogenic diet has a number of characteristic metabolic effects including increased ketone body formation and elevated plasma levels of medium chain fatty acids. There is no known correlation between ketone body levels and seizure control, and relatively little research has been carried out on the effects of the increased fatty acid concentrations.

We have determined that decanoic acid, a medium chain fatty acid that increases in plasma concentration as a result of a ketogenic diet in which MCT forms a part, has a direct effect on mitochondrial function and availability in cells in vitro.

Thus, decanoic acid may be beneficial for the treatment of epilepsy, particularly in patients who currently require a ketogenic diet; diseases associated with inherited mitochondrial dysfunction; and patients with acquired mitochondrial disorders, including those with diabetes, Parkinson's disease and dementias including Alzheimer's disease.

STATEMENTS OF THE INVENTION

According to a first aspect of the present invention there is provided a composition suitable for human consumption comprising a decanoic acid to octanoic acid ratio of 2:1 wt/wt or is substantially free from octanoic acid and optionally is substantially free from any other saturated fatty acid.

In other embodiments the decanoic acid to octanoic acid ratio is at least 2:1 wt/wt, at least 3:1 wt/wt, at least 4:1 wt/wt, at least 5:1 wt/wt, at least 6:1 wt/wt, at least 9:1 wt/wt, at least 10:1 wt/wt, at least 15:1 wt/wt, at least 20:1 wt/wt, at least 30:1 wt/wt, at least 40:1 wt/wt, at least 50:1 wt/wt, at least 60:1 wt/wt, at least 70:1 wt/wt, at least 80:1 wt/wt, at least 85:1 wt/wt, at least 90:1 wt/wt, at least 95:1 wt/wt, at least 98:1 wt/wt or at least 99:1 wt/wt. Thus, in one embodiment the composition is free from or substantially free from octanoic acid.

In one embodiment the decanoic acid is greater than 50%, 51%, 52%, 53%, 54%, 55%, 56%, 57%, 58% or 59% of the total weight of fatty acid content, at least 60% of the total weight of fatty acid content, at least 65% of the total fatty acid content, at least 70% of the total weight of fatty acid content, at least 80% of the total weight of fatty acid content, at least 90% of the total weight of fatty acid content, or is at least 99%, or 100% of the total weight of fatty acid content. Thus the present invention may make use of a product which comprises pure or substantially pure decanoic acid.

Thus the present invention also envisages a composition which is free from or substantially free from mono- or poly-unsaturated fatty acids.

According to a second aspect of the present invention there is provided a composition suitable for human consumption which has a ketogenic ratio of from 0.2 to 0.3:1. Other embodiments include, but are not limited to, ratios of 0.5:1, 1:1 to 5:1, preferably up to 4:1, and wherein the majority of fat is decanoic acid. In one embodiment this composition has a ketogenic ratio of 2:1 to 4:1. By "ketogenic ratio" we refer to the ratio of the weight of lipid to the sum of the weights of carbohydrate and protein.

According to a third aspect of the present invention there is provided a composition suitable for human consumption comprising proteins, fat and carbohydrates, which provides 2500 to 3100 kJ per 100 g dry mass, and wherein at least 50% of the fat is decanoic acid.

In one embodiment of the composition of the third aspect of the present invention at least 55%, 60%, 65%, 70%, 75%, 80%, 85%, 90% 95%, 98%, 99% or 100% of the fat is decanoic acid.

In one embodiment of the composition of the third aspect of the present invention the composition does not include any mono- and/or polyunsaturated fatty acid.

In one embodiment of the composition of the invention provides 2520 to 3780 kJ per 100 g dry mass. In another embodiment of the composition of the invention provides 2520 to 3180 kJ per 100 g dry mass.

In one embodiment of the compositions of the invention the weight amounts of lipid to the sum of proteins and carbohydrates is 1.0 to 1, 2.0 to 1, 5.0 to 1, or say 2.0-5.0 to 1, or 2.4-4.0 to 1, or 2.6-3.8 to 1.

In one embodiment of the compositions of the invention, the composition is in the form of a human food stuff.

In one embodiment of the compositions of the invention, the composition is in a form for delivering a dosage of at least about 5 g/l to 150 g/l decanoic acid per day. In alternative embodiments the dosage is about 5 g/l, 10 g/l, 15 g/l, 20 g/l, 30 g/l, 40 g/l, 50 g/l, 60 g/l, 70 g/l, 80 g/l, 90 g/l, 100 g/l, 110 g/l, 120 g/l, 130 g/l, 140 g/l, 150 g/l, 175 g/l, 200 g/l, 225 g/l, 250 g/l or 500 g/l decanoic acid per day.

In one embodiment of the compositions of the invention, the composition is in the form of a complete nutritional product.

In one embodiment of the compositions of the invention, the composition is in powdered form.

In one embodiment of the compositions of the invention, the composition is in a spray dried form.

In one embodiment of the compositions of the invention, the composition is in a form suitable for fortifying food or drink.

In one embodiment of the compositions of the invention, the composition is in the form of a food stuff.

In one embodiment of the compositions of the invention, the composition is in the form of an oil-in-water emulsion.

The compositions according the present invention may be in the form of an oil, mayonnaise, margarine, low fat spread, a dairy product including yoghurts, a cheese spread, processed cheese, a dairy dessert, a flavoured milk, cream, a fermented milk product, cheese, butter, a condensed milk product, an ice cream mix, a soya product, pasteurised liquid egg, a bakery product, a confectionary product, confectionary bar, chocolate bar, high fat bar, liquid emulsion, spray dried powder, freeze dried powder, UHT pudding, Pasteurised pudding, gel, jelly, yoghurt or a food with a fat-based or water-containing filling.

According to a fourth aspect of the present invention there is provided use of decanoic acid for the preparation of a medicament for the treatment of a disease associated with mitochondria dysfunction. For the avoidance of doubt by "medicament" we include any of the compositions of the present invention, including a nutritional supplement or complete nutritional product.

According to a fifth aspect of the present invention there is provided decanoic acid for the treatment of a disease associated with mitochondria dysfunction.

Thus we provide the use of decanoic acid according to the present invention wherein the disease is epilepsy, diabetes, Parkinson's disease, dementias including Alzheimer's disease, or an inborn error of mitochondrial function.

Thus we also provide the use of decanoic acid according to the present invention wherein the treatment of epilepsy includes the control of seizures.

According to a sixth aspect of the present invention there is provided a method for the treatment or prevention of a disease associated with mitochondria dysfunction comprising administering an effective amount of decanoic acid to a patient in need of the same.

According to a seventh aspect of the present invention there is provided a method of affecting the cellular content of mitochondria comprising administering decanoic acid to the cell.

According to an eighth aspect of the present invention there is provided a method of affecting the cellular function of mitochondria comprising administering decanoic acid to the cell.

According to a ninth aspect of the present invention there is provided a method of affecting the cellular availability of mitochondria comprising administering decanoic acid to the cell.

According to a tenth aspect of the present invention there is provided a method of modulating the cellular energy supply comprising administering decanoic acid to the cell.

A method according to any one of the sixth to tenth aspects of the invention wherein the disease is epilepsy, diabetes, Parkinson's disease, dementias including Alzheimer's disease, or an inborn error of mitochondrial function.

In one embodiment the treatment of epilepsy includes the control of seizures.

According to a eleventh aspect of the present invention there is provided decanoic acid, a method or use according to any one of the fourth to tenth aspects of the invention wherein the decanoic acid is administered in the form of a composition according to any one of the first to third aspects of the invention.

According to a twelfth aspect of the present invention there is provided decanoic acid, the method or use according to any one of the fourth to tenth aspects of the invention in which a dosage of at least about 5 g/l to 250 g/l or at least about 5 g/l to 500 g/l decanoic acid is administered per day.

In general terms therefore the present invention can be summarised as relating to decanoic acid for use in the treatment of a disease associated with mitochondria dysfunction.

Decanoic acid is also known as capric acid and is a saturated fatty acid of formula $CH_3(CH_2)_8COOH$. It is also referred to herein as "C10".

BRIEF DESCRIPTION OF THE FIGURES

FIG. 1 illustrates the dose-response curve over a six day incubation period.

FIG. 2 illustrates the effect of 250 µM C10 for six days on Complex I activity.

FIG. 4 is an electron microscopy illustrating the increase in number of mitochondria cells.

FIG. 5 is electron microscopy data illustrated graphically.

DETAILED DESCRIPTION

Figure 3:
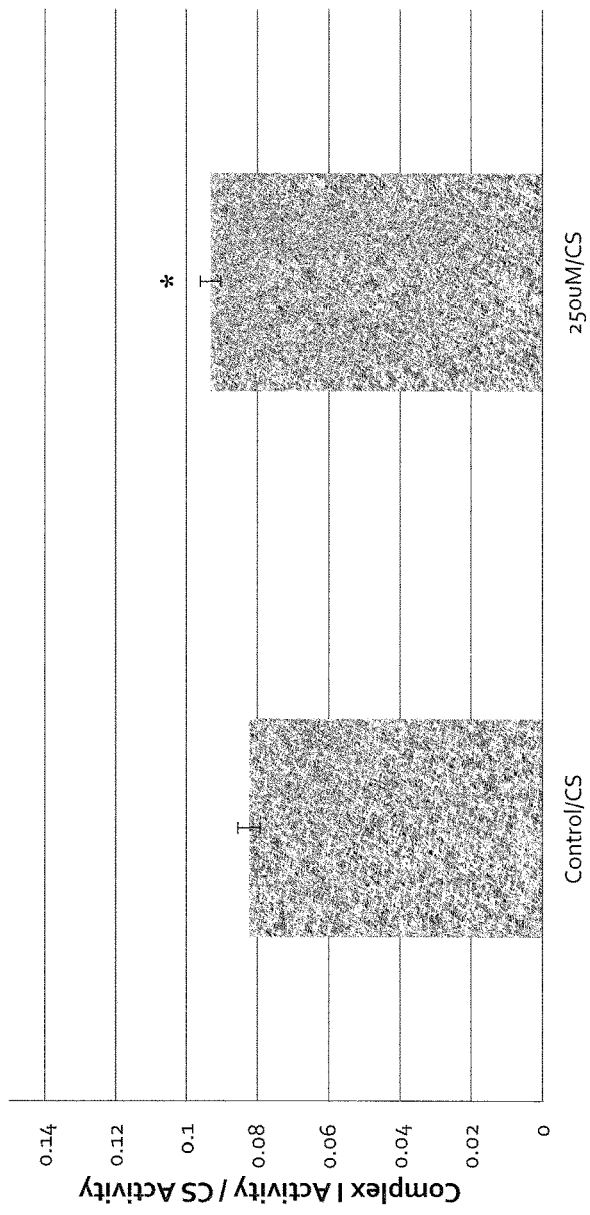
FIG. 3 illustrates the effect of 250 µM C10 for six days on Complex I activity—normalised against CS.

By elucidating the mechanism associated with the benefits of ketogenic diets we overcome some of the problems associated with prior compositions by providing a highly effective product which can be formulated to increase its palatability and deliver a specific level of C10. Moreover it allows diseases to be treated by the use of C10 outside of the strict confines of the classic ketogenic diet.

Briefly, the classical version of the ketogenic diet uses ratios to determine and describe fat content. Thus, the ketogenic ratio represents the relationship between the grams of fat and the combined grams of protein and carbohydrate. In a 4:1 ratio there are four times as many grams of fat for every 1 g of protein and carbohydrate combined. The ratio is traditionally intended to regulate the degree of ketosis, with higher ratios theoretically stimulating greater ketosis. The MCT version of the ketogenic diet uses percentage energy from fat to determine and describe fat content. The other two versions of the ketogenic diet are the so-called modified Atkins diet and the low glycaemic (GI) index diet, which encourage people to ingest a lot of fat. In these two latter diets neither the ratio nor the percentage of fat is formally calculated although typically the ketogenic ratio is about 1:1. In all 4 versions of the ketogenic diet the percentage of total energy from fat ranges from 50-92% but is typically 70-90%. In any event whichever form of the diet one follows it is necessary to ingest a lot of fat to achieve efficacy and this can impact severely on patient compliance. However, following the teaching of the present invention it may be possible to arrive at a clinical benefit with a diet which is outside these traditional ratios provided that the fat content contains suitable levels of decanoic acid according to the present invention.

If the invention is delivered as part of a ketogenic diet, the ratio or total fat content can be altered during therapy to achieve nutritional goals and to optimize clinical benefit. The ratio can be in the range of 1.0:1, 1.5:1, 2.0:1, 2.5:1, 3.0:1, 3.5:1, 4.0:1, 4.5:1 or 5.0:1.

In one embodiment the ratio is 2.25:1 to 3.9:1. In another embodiment the ratio is 2.26 to 3.8:1 or 2.7-3.4:1. In further embodiments the ratio is 3.21:1, 3.23:1, 3.24:1, 3.25:1, 3.26:1, 3.27:1, 3.28:1 or 3.29:1.

It should be borne in mind that two different individuals of the same age and weight may experience a different level of clinical benefit on the same ratio or quantity of fat. Thus a clinician may wish to alter the ratio to achieve the optimum clinical benefit. Thus fine tuning the ratio or total fat content and altering it at the start and end of therapy, and during the therapy, e.g. to increase compliance, is within the scope of the invention.

Decanoic acid occurs naturally in e.g. coconut oil and palm kernel oil and it can be envisaged that these products could form the key basis of the diet. In general terms decanoic acid forms around 5 to 8% of the fatty acid composition of coconut oil. Thus one can envisage a food composition in which the fatty acid composition comprises from about 5 to 8% of decanoic acid. Conversely octanoic acid comprises around 4.6 to 10% of the fatty acid composition of coconut oil. Since the present invention has identified that C8 is less beneficial than C10, one can envisage a food composition which the fatty acid composition comprises less than 10%, ideally less than 4.6% of octanoic acid.

It will be appreciated that the lipid fraction useful in the present invention can be in the form of triglycerides, diacylglycerides, monoacyl-glycerides, phospholipids, lyso-phospholipids, cholesterol and glycolipids, with triglycerides being generally preferred.

One can envisage the situation where the C10 is delivered to a patient as a blended product. In this case it will be appreciated that according to the present invention the amount of saturated fatty acids utilised is relatively high. In particular it is preferably between 23 and 50, more preferably 25-45, and even more preferably 33-44 g per 100 g lipids, on fatty acid basis. The saturated fatty acids have 8 to 24 carbon atoms. It is preferred that a major part of the saturated fatty acids is decanoic acid (C10:0). Decanoic acid thus provides e.g. 15-50, preferably 18-45, more preferably 23-44 g per 100 g lipids. A particular embodiment comprises 30-37 g decanoic acid per 100 g lipids. Coconut oil or palm oil is a preferred source for at least 50%, preferably between 70 and 90 of the lipid fraction. The remainder of the lipid fraction can be selected from e.g. medium-chain triglyceride sources such as fractionated coconut oil, macadamia oil, palm oil or palm kernel oil, or long-chain triglyceride sources such as safflower oil, sesame seed oil, soy oil (which may be obtained from soybean), sunflower oil, high oleic sunflower oil, corn oil, canola oil, walnut oil, evening primrose oil, peanut oil, cottonseed oil, rapeseed oil, olive oil, fish oil, palm olein or algal oil, or mixtures thereof, preferably soybean oil (preferably between 2 and 30), medium-chain triglycerides (with fatty acids having 8-12 carbon atoms; between 0 and 14), marine oils (preferably between 0 and 14 wt. %, more preferably between 2 and 12 wt. %), and phospholipids, mono- and di-glycerides.

The present invention preferably does not include mono-unsaturated and/or polyunsaturated fatty acids. However, if present the amount of mono-unsaturated fatty acids is suitably between 25 and 48, preferably 28-43, more preferably 30-40 g per 100 g lipids (fatty acid basis). If present, the amount of polyunsaturated fatty acids (i.e. having two or more unsaturated bonds), to which the trans fatty acids have been excluded, is 16-40, preferably 20-30 g per 100 g lipids. It is preferred that the lipid fraction also comprises omega.-3 polyunsaturated fatty. In particular, the polyunsaturated fatty acids comprise more than 0.5, preferably 1.0-10 wt. %. The amount of trans fatty acids is below 20, preferably 0-10, more preferably 0.2-4 g per 100 g lipids.

MCT oil is a food grade oil generally comprising more than 90 wt % fatty acids. Traditionally these fatty acids have been made up of saturated fatty acids having 8, 10 or 12 carbon atoms. Whilst MCT oil may have application in the present invention, preferred is the use of MCT based oil in which the majority of the saturated fatty acids are decanoic acid.

Preferably decanoic acid represents at least 51%, 55, 60, 65, 70, 75, 80, 85, 90, 95 or 100 wt % of the fatty acid content of the composition useful in the present invention.

In one embodiment of the composition useful in the present invention the ratio of the saturated fatty acids of C10 to C8 is 60:40, 65:35, 70:30, 75:25, 80:20, 85:15, 90:10, 95:5 or 100:0.

LCT oil is defined as a food grade oil that comprises 15% of fatty acids having 20 or more carbon atoms. The present invention may utilise an LCT oil, but preferably at a level of 1%, 0.5% or 0.1% or less per 100 g.

In general terms, administration of the composition of C10 of the present invention may be by an oral route or another route into the gastro-intestinal tract or by parenteral routes. The forms for these modes of administration may include conventional forms, either as liquid solutions or suspensions, solid forms suitable for solution or suspension in liquid prior to injection, or as emulsions.

Thus, the composition of C10 of the present invention can be formulated in a suitable form, which may be a dosage form. The form is generally suitable for oral administration, but the invention is also applicable to gastric tube feeding. Suitable forms may include tablets, dragees, capsules, gel caps, powders, granules, solutions, emulsion, suspension, coated particles, spray-dried particles and pills, which contain the composition of C10 of the present invention, and optionally one or more suitable pharmaceutically acceptable carriers. In some embodiments the composition of C10 can be inserted or mixed into a food substance. In some embodiments the composition of C10 of the present invention is in the form of a nutritional product. By nutritional product we generally refer to the situation where the substance intended to supplement a diet; although in the present situation the composition may be in a form such that it is intended to be the sole item or a meal or diet, i.e. a so-called "complete" nutritional product. Thus, the present invention may be administered to subjects in the form of nutritional supplements, foods, beverages. A preferred type of food is a medical food, e.g. a food which is in a formulation to be consumed under medical supervision and which is intended for the specific dietary management of a disease or condition, such as in the ketogenic diet referred to above.

As mentioned above, the present invention may be realised in the form of a product which is suitable for complete nourishment of human beings, or as an oil emulsion or supplement or any other convenient product form. The product may be suitable for infants, children and adults. The product as well as comprising a lipid fraction in accordance with the teachings of the present invention may optionally comprise a protein fraction, a fraction of digestible carbohydrates, available and/or nonavailable carbohydrates, a nitrogen fraction and optionally, a vitamin fraction, a mineral/trace element fraction or other components as may be appropriate to provide a nutritional supplement or complete nutritional product.

The protein fraction comprises preferably peptides larger than 8 amino acids, which can make the product unsuitable for parenteral administration, due to potential allergic reactions. It is preferred to select proteins, which have strong emulgating properties, such as certain caseins. However, products usable for reconstitution in water or liquid formula should preferably contain lysolecithin, tartaric esters or combinations thereof as stabilization system in order to obtain a product that is suitable for drinking.

The product may preferably be solid or semi-solid, such as a powder, bar, pudding, etcetera. A semi-solid product is understood to be a product having a solid content of more than 40 g per 100 g ready to use product. More preferably the semi-solids are supplied as powder, which can be reconstituted in water to be used as a single, complete food. The powder may comprise of primary particles, agglomerated primary particles or mixtures of particles of various size. Such powders can be manufactured using methods known in the art, such as spray drying. Spray drying is preferred when aids are used to improve flowing characteristics. The product may also be in the form of an oil which could be used for frying etc.

The dry product may be at least partly soluble in water, so as to allow ready make-up of a liquid food, if desired. Preferably at least 50 wt %, more preferably at least 75 wt % of the dry mass is soluble when dissolved as 10% (w/v) in water at 20° C.

The amount of digestible carbohydrates is 0-9, preferably 3.2-9, more preferably 4-8.6, even more preferably 5-8.2 g per 100 g dry mass. The amount of protein is 5-20, preferably 13-20, more preferably 13-18, more preferably 13.8-17, even more preferably 14.2-16.2 g per 100 g dry mass. The amount of lipids is 0, 0.1-100 g per 100 g dry mass, but may be 60-80, 63-75, or 65-72 g per 100 g dry mass.

The inclusion of alpha-lactalbumin or ingredients which comprise high amounts of protein, are particularly suitable. The presence of more than 20 wt % alpha-lactalbumin in the protein fraction of the product results in easy compliance with the requirements for leucine, lysine, methionine and cysteine, excellent palatability and digestion properties. Preferably more than 20%, more preferably 40-80 wt % of the protein fraction consists of alpha-lactalbumin.

The digestible carbohydrate fraction can comprise food grade ingredients such as glucose syrup, maltodextrins, lactose, sucrose, galactose, ribose, etc. Though excellent products can be obtained in terms of efficacy when several of the other technical features as disclosed in this description are applied, best results in terms of avoidance of side effects and efficacy are obtained if the digestible carbohydrate fraction takes a specific form. It appears beneficial if at least 20%, preferably 30-90% of the digestible carbohydrate fraction is formed by a source of galactose or ribose. Lactose is considered as suitable ingredient for this purpose. In particular oxidative stress will decrease, when such ketogenic formula is consumed, which comprises such non-glucose digestible carbohydrates. Digestibility is determined by applying the Englyst 1999 method.

The proteins, lipids, and carbohydrates preferably originate from at least two different sources, for example, the proteins at least partly from animal, especially milk, source, but optionally also partly from plant source, the lipids at least partly from vegetal source, and the carbohydrates at least partly from milk source, or from a combination of milk (lactose) and plant (glucose, maltodextrins etc.).

The amount of micro ingredients follow recommendations. However, increasing the amounts of several specific ingredients above recommendations improves efficacy and prevents side effects in paediatric epileptics.

In order to maintain normal development and growth, the energy requirement may be calculated according to an individual's energy requirements. Useful products for feeding patients, particularly paediatric epileptic patients, have an energy density of 3.8-12.6 kJ/ml preferably 4.6-8.4 kJ/ml and more preferably 5.0-7.2 kJ/ml. An energy density of 5.4-6.7 kJ/ml appears particularly useful when nourishing completely with the product. When the energy density of the liquid formula is 8.4-12.6 kJ/ml, the product may also be useful for intermediate fortification of the patient.

The product usefully is relatively energy dense. In some embodiments, it provides 2520-3780, or say 2520-3080, and preferably 2800-3040 kJ per 100 grams dry matter. The diet may provide 2500-3100 kJ per 100 grams dry matter, such as 2505, 2510, 2515, 2520, 2525, 2530, 2535 or 2540 to 3100, 3095, 3090, 3085 or 3080 kJ per 100 g. In a particularly preferred embodiment the diet comprises 2984, 2985, 2986, 2987, 2988, 2989 or 2990 kJ per 100 g.

The product, suitably after reconstitution to a liquid product, can be administered in an amount of between 50 and 200, preferably between 75 and 150 g per day, calculated as dry mass, for infants younger than 12 months, following general energy consumption recommendations, like has been described in the guidelines of the health authorities. For older children, the preferred daily amount calculated on dry mass is between 100 and 360, especially between 150 and 300 g. For adults these amounts are 100-500, most preferably 150-340 g for providing most ketogenic potential, and at the same time a sufficient amount of essential amino acids, carbohydrate skeletons, and other nutrients and being well tolerated and safe.

Examples of suitable products for use in the present invention are given below:

| Spray Dried Powder Formulation Nutrition Information | | |
|---|---|---|
| | | per 100 g |
| Energy | kj | 2987 |
| | kcal | 714 |
| Protein | g | 16 |
| Total carbohydrate | g | 7.0 |
| sugars | g | 0.7 |
| Total fat | g | 75 |
| saturates | g | 75 |
| monounsaturates | g | 0 |
| polyunsaturates | g | 0 |
| C10 | g | 74.9 |
| Other lipids | g | 0.1 |
| Linoleic acid | mg | 0 |
| α-linolenic acid | mg | 0 |
| Fibre | g | 0 |
| Minerals | | |
| Sodium | mg | 245 |
| | mmol | 10.5 |
| Potassium | mg | 1.7 |
| | mmol | <0.1 |
| Chloride | mg | 1.5 |
| | mmol | <0.1 |
| Calcium | mg | 8.8 |
| | mmol | 0.2 |
| Phosphorus | mg | 140 |
| | mmol | 4.5 |
| Magnesium | mg | 0.7 |
| | mmol | 0.3 |

| Powder Formulation NUTRITIONAL INFORMATION | | | |
|---|---|---|---|
| | | per 100 g | per 100 ml (25%) |
| Energy | kJ | 2508 | 627 |
| | kcal | 600 | 150 |
| Protein | g | 22.0 | 5.5 |
| Carbohydrate | g | 14.8 | 3.7 |
| Fat | g | 53.8 | 13.5 |
| of which C10 | g | 36.0 | 9.0 |
| of which other lipids | g | 17.0 | 4.3 |
| Fibre | g | 6.0 | 1.5 |
| Vitamins | | | |
| Vitamin A | µg | 293 | 58.6 |
| Vitamin D | µg | 5.6 | 1.12 |
| Vitamin E | mg | 5.6 | 1.12 |
| Vitamin C | mg | 33.3 | 6.7 |
| Vitamin K | µg | 37.7 | 7.5 |
| Thiamin | mg | 0.44 | 0.09 |
| Riboflavin | mg | 0.66 | 0.13 |
| Niacin | mg | 6.6 | 1.32 |
| Vitamin B6 | mg | 0.6 | 0.12 |
| Folic Acid | µg | 149 | 29.8 |
| Vitamin B12 | µg | 0.85 | 0.17 |
| Biotin | µg | 11.3 | 2.26 |
| Pantothenic acid | mg | 2.2 | 0.44 |
| Choline | mg | 203 | 40.6 |
| Minerals | | | |
| Sodium | mg | 444 | 88.8 |
| | mmol | 19 | 3.8 |
| Potassium | mg | 600 | 120 |
| | mmol | 15 | 3 |
| Chloride | mg | 555 | 111 |
| | mmol | 15.5 | 3.1 |
| Calcium | mg | 480 | 96 |
| Phosphorus | mg | 444 | 88.8 |
| Phosphate | mmol | 14.2 | 2.84 |
| Magnesium | mg | 124 | 24.8 |
| | mmol | 5.1 | 1.02 |
| Trace Elements | | | |
| Iron | mg | 5.55 | 1.11 |
| Copper | mg | 0.44 | 0.088 |
| Zinc | mg | 4.4 | 0.88 |
| Manganese | mg | 0.74 | 0.148 |
| Iodine | µg | 55.5 | 11.1 |
| Molybdenum | µg | 26.4 | 5.32 |
| Selenium | µg | 27.4 | 5.48 |
| Chromium | µg | 13.2 | 2.64 |

| Ketogenic Feed | | | |
|---|---|---|---|
| | | per 100 g | per 100 ml (25%) |
| Energy | kj | 2508 | 627 |
| | kcal | 600 | 150 |
| Protein | g | 30 | 7.5 |
| Carbohydrate | g | 15 | 3.8 |
| Fat | g | 48.6 | 12.2 |
| of which MCT | g | 25.3 | 6.3 |
| of which LCT | g | 23.3 | 5.8 |
| Fibre | g | 0 | 0 |
| Vitamins | | | |
| Vitamin A | µg | 93 | 58.6 |
| Vitamin D | µg | 5.6 | 1.12 |
| Vitamin E | mg | 5.6 | 1.12 |
| Vitamin C | mg | 33.3 | 6.7 |
| Vitamin K | µg | 37.7 | 7.5 |
| Thiamin | mg | 0.44 | 0.09 |
| Riboflavin | mg | 0.66 | 0.13 |
| Niacin | mg | 6.6 | 1.32 |

-continued

| Ketogenic Feed | | | |
|---|---|---|---|
| | | per 100 g | per 100 ml (25%) |
| Vitamin B6 | mg | 0.6 | 0.12 |
| Folic Acid | µg | 149 | 29.8 |
| Vitamin B12 | µg | 0.85 | 0.17 |
| Biotin | µg | 11.3 | 2.26 |
| Pantothenic acid | mg | 2.2 | 0.44 |
| Choline | mg | 203 | 40.6 |
| Minerals | | | |
| Sodium | mg | 444 | 88.8 |
| | mmol | 19 | 3.8 |
| Potassium | mg | 600 | 120 |
| | mmol | 15 | 3.0 |
| Chloride | mg | 555 | 111 |
| | mmol | 15.5 | 3.1 |
| Calcium | mg | 480 | 96 |
| | mmol | 12 | 2.4 |
| Phosphorus | mg | 444 | 88.8 |
| | mmol | 14.2 | 2.84 |
| Magnesium | mg | 124 | 24.8 |
| | mmol | 5.1 | 1.02 |
| Trace Elements | | | |
| Iron | mg | 5.55 | 1.11 |
| Copper | mg | 0.44 | 0.088 |
| Zinc | mg | 4.4 | 0.88 |
| Manganese | mg | 0.74 | 0.148 |
| Iodine | µg | 55.5 | 11.1 |
| Molybdenum | µg | 26.6 | 5.32 |
| Selenium | µg | 27.4 | 5.48 |
| Chromium | µg | 13.2 | 2.64 |

| NUTRITIONAL INFORMATION | | | |
|---|---|---|---|
| | | per 100 ml | per carton (250 ml) |
| Emulsion | | | |
| Energy | kJ | 848 | 2121 |
| | kcal | 180 | 449 |
| Total protein | g | 0 | 0 |
| Carbohydrate | g | 0 | 0 |
| Fat | g | 21.5 | 53.8 |
| of which saturates | g | 21 | 52.5 |
| of which monosaturates | g | 0.3 | 0.8 |
| of which polyunsaturates | g | 0.2 | 0.5 |
| of which other lipids | g | 1.5 | 3.8 |
| of which C10 | g | 20 | 50 |
| Vitamins | | | |
| Vitamin A | µg | <21 | <53 |
| Minerals | | | |
| Sodium | mg | 39 | 97 |
| | mmol | 1.7 | 4.3 |
| Fatty Acids | | | |
| Linoleic Acid | mg | 140 | 350 |
| Alpha LinolenicAcid (18:3) | mg | 60 | 150 |

| 50% Emulsion | | | |
|---|---|---|---|
| | | Per 100 ml | per 250 ml carton |
| Energy | kJ | 1743 | 4358 |
| | kcal | 415 | 1038 |
| Protein | g | 0 | 0 |
| Total Carbohydrate | g | 0 | 0 |
| sugars | g | 0 | 0 |

| NUTRITIONAL INFORMATION | | | |
|---|---|---|---|
| Total Fat | g | 50 | 125 |
| of which medium chain triglycerides | g | 50 | 125 |
| of which long chain triglycerides | g | 0 | 0 |

EXPERIMENTAL EXAMPLES

Brief Experimental Approach

Mitochondrial enrichment was estimated by evaluation of citrate synthase activity (corrected for total cellular protein content). This enzyme is localised at the mitochondria, comprises part of the TCA cycle and is commonly used as a marker of mitochondrial enrichment.

In order to gain further independent insight into mitochondrial function, the activity of the respiratory chain enzyme, Complex I, was also evaluated.

A human neuroblastoma cell line (SH-SY5Y) was utilised throughout this study, except where stated. In brief, cells were exposed to a range (50-300 µM, dissolved in 0.5% DMSO) of either octanoic or decanoic acid concentrations. After 6 days, the cells were harvested and citrate synthase activity was determined. Activity was expressed as nmol/min/mg of cellular protein.

In a second experiment, cells were exposed to decanoic acid (250 µM, dissolved in 0.5% DMSO) for 6 days. The cells were subsequently harvested, and the activity of Complex I was determined. Each experiment was repeated 5 times, and the activity was expressed as nmol/min/mg of cellular protein.

Additionally, SH-SY5Y cells were prepared for electron microscopy (EM) analysis to assess mitochondrial density and morphology following treatment with decanoic acid.

Finally, the effect of decanoic acid was validated in an independent cell line. Primary cultures of human fibroblasts were exposed to decanoic acid at a concentration of 250 µM for 6 days. Following the incubation, citrate synthase activity was again assessed.

Results

Octanoic acid had no effect on the parameters studied. However, exposure of the SH-SY5Y cells to decanoic but not octanoic acid resulted in an increase in citrate synthase activity when compared to control cells (incubated with vehicle only). This effect was dose dependent (FIG. 1), with a maximum, highly significant ($p<0.001$), 30% increase occurring at a concentration of 250 µM (expressed as nmol/min/mg cell protein):

| Control (n = 8) | Decanoic Acid (n = 8) |
|---|---|
| 105 ± 5 | 137 ± 5 |

Determination of Complex I activity in SH-SY5Y cells also revealed a significant ($p<0.002$) increase with respect to the control experiment, following treatment with decanoic acid (FIG. 2). A significant ($p<0.05$) increase in Complex I activity was still apparent when the data were normalised against citrate synthase activity (FIG. 3). Normalisation takes into account the mitochondrial enrichment following administration of decanoic acid. The Complex I:citrate synthase activity ratio therefore provides a more accurate demonstration of mitochondrial function independently of mitochondrial content.

In all cases, the addition of 0.5% DMSO was shown to have no effect on the parameters studied, i.e. when compared to untreated cells.

The electron microscopy study revealed increased numbers of mitochondria in cells treated with 250 µM decanoic acid (FIG. 4). The mitochondria are clearly visible in both images as dark circular and elongated organelles present in the cytoplasm. Treatment with decanoic acid also appears to alter the morphology of the mitochondria, with the more intense staining potentially resulting from more dense cristae within the organelles. These observations are supported by a quantitative analysis (FIG. 5) of the EM data, which reveals a significant ($p<0.002$) increase in the number of mitochondria per cell.

Finally, the data were validated by the observation that primary human fibroblasts exposed to decanoic acid (250 µM) also revealed a 45% increase in citrate synthase activity.

CONCLUSIONS

At a concentration relevant to that achieved in the plasma by patients on the ketogenic diet, decanoic acid exposure resulted in a marked increase in citrate synthase activity in treated SH-SY5Y neuroblastoma cells. Activity of this enzyme is known to correlate with cellular mitochondrial levels, therefore these findings raise the possibility that decanoic acid exposure leads to an alteration in cellular mitochondrial function, potentially by increasing mitochondrial content. This conclusion is further supported by independent data derived from EM-based direct observation of cellular mitochondrial content. Additionally, Complex I activity was observed to increase following administration of decanoic acid. This mitochondrial respiratory enzyme is a direct marker of mitochondrial function, therefore this data independently suggests an increase in mitochondrial function results from incubation with decanoic acid. Notably, these findings do not appear to be restricted to one cell type since a similar phenomenon, with regards to increased citrate synthase activity, was apparent in primary human fibroblast cells exposed to decanoic acid.

This action of decanoic acid may therefore prove to be of therapeutic benefit for those patients with epilepsies that are responsive to the ketogenic diet. Similarly, for patients with inherited or acquired mitochondrial disorders, decanoic acid may also be beneficial. With regards to acquired disorders, this could include diabetes and neurodegenerative conditions such as Parkinson's disease and dementias including Alzheimer's disease.

It will be appreciated that any of the ranges disclosed herein may be used in suitable combinations.

The invention claimed is:

1. A method for treatment of a disease associated with mitochondria dysfunction, the method comprising administering to an individual having the disease a composition comprising an effective amount of a combination of decanoic acid and octanoic acid having a weight ratio of the decanoic acid to the octanoic acid of at least 2:1.

2. The method according to claim 1 wherein the disease is selected from the group consisting of epilepsy, diabetes, Parkinson's disease, dementias including Alzheimer's disease, and an inborn error of mitochondrial function.

3. The method according to claim 2 wherein the treatment of epilepsy includes control of seizures.

4. A method of affecting at least one characteristic selected from the group consisting of cellular content of mitochondria, cellular function of mitochondria, cellular availability of mitochondria, and modulating cellular energy supply of a cell, the method comprising administering to the cell a composition comprising an effective amount of a combination of decanoic acid and octanoic acid having a weight ratio of the decanoic acid to the octanoic acid of at least 2:1.

5. The method according to claim 1 in which a dosage of about 5 g/l to 500 g/l of the decanoic acid is administered to the individual per day.

6. The method according to claim 1 wherein the decanoic acid is greater than 50% of the total weight of fatty acid content of the composition.

7. The method according to claim 1 wherein the composition is substantially free from any other saturated fatty acid.

8. The method according to claim 1 wherein the composition is substantially free from mono- and poly-unsaturated fatty acids.

9. The method according to claim 1 wherein the weight ratio of the decanoic acid to the octanoic acid is at least 3:1.

10. The method according to claim 1 wherein the weight ratio of the decanoic acid to the octanoic acid is at least 4:1.

11. The method according to claim 1 wherein the weight ratio of the decanoic acid to the octanoic acid is at least 5:1.

12. The method according to claim 1 wherein the weight ratio of the decanoic acid to the octanoic acid is at least 6:1.

13. The method according to claim 1 wherein the weight ratio of the decanoic acid to the octanoic acid is at least 9:1.

14. The method according to claim 1 wherein the weight ratio of the decanoic acid to the octanoic acid is at least 10:1.

15. The method according to claim 1 wherein the weight ratio of the decanoic acid to the octanoic acid is at least 20:1.

16. The method according to claim 1 wherein the decanoic acid is at least 60% of the total weight of fatty acid content of the composition.

17. The method according to claim 1 wherein the decanoic acid is at least 70% of the total weight of fatty acid content of the composition.

18. The method according to claim 1 wherein the decanoic acid is at least 80% of the total weight of fatty acid content of the composition.

19. The method according to claim 1 wherein the decanoic acid is at least 90% of the total weight of fatty acid content.

20. The method according to claim 1 wherein the composition has an energy density of 2500 to 3100 kJ per 100 g dry mass.

21. The method according to claim 1 wherein the composition has an energy density of 2540 to 3080 kJ per 100 g dry mass.

22. The method according to claim 1 wherein the composition has a ketogenic ratio from 2.7:1 to 3.4:1.

23. The method according to claim 1 wherein the composition comprises the octanoic acid in an amount less than 10 wt. %.

24. The method according to claim 1 wherein the composition comprises 33-44 g total saturated fatty acids per 100 g lipids.

25. The method according to claim 1 wherein the composition comprises 30-37 g of the decanoic acid per 100 g lipids.

26. The method according to claim 1 wherein the composition comprises coconut oil or palm oil as 70-90 wt. % of total lipids.

27. The method according to claim 1 wherein the composition comprises 5-8.2 g carbohydrates per 100 g dry mass of the composition.

28. The method according to claim 1 wherein the composition comprises 14.2-16.2 g protein per 100 g dry mass of the composition.

29. The method according to claim 28 wherein 40-80 wt. % of the protein is alpha-lactalbumin.

30. The method according to claim 1 wherein the composition comprises 65-72 g lipids per 100 g dry mass of the composition.

31. The method according to claim 1 wherein the composition is administered to the individual daily for at least six days.

32. The method according to claim 1, wherein the decanoic acid is at least 99% of the total weight of fatty acid content of the composition.

33. The method according to claim 4, wherein the decanoic acid is at least 99% of the total weight of fatty acid content of the composition.

* * * * *